United States Patent [19]

Friedland et al.

[11] Patent Number: 4,828,113

[45] Date of Patent: May 9, 1989

[54] DENTAL TREATMENT KIT

[76] Inventors: Jeffrey B. Friedland, 6 Magnolia La., Woodbury, N.Y. 11797; Arthur Adelberg, 21 Avondale Rd., Plainview, N.Y. 11803; Barry M. Deitch, 10 Astro Pl., Dix Hills, N.Y. 11746

[21] Appl. No.: 195,718

[22] Filed: May 18, 1988

[51] Int. Cl.[4] .............................................. B65D 85/00
[52] U.S. Cl. ..................... 206/570; 206/63.5; 206/369; 206/459
[58] Field of Search ...................... 206/63.5, 369, 370, 206/438, 459, 564

[56] References Cited

U.S. PATENT DOCUMENTS

| | | | |
|---|---|---|---|
| 1,644,830 | 10/1927 | Henderson | 206/370 |
| 1,680,804 | 8/1928 | Remley | |
| 2,447,844 | 8/1948 | Cutter | |
| 2,740,516 | 4/1956 | Renn | |
| 3,460,252 | 8/1969 | Schneider et al. | |
| 3,464,111 | 9/1969 | Gillard | |
| 3,777,882 | 12/1973 | McIntyre | 206/370 |
| 3,802,555 | 4/1974 | Grasty et al. | 206/370 |
| 3,981,398 | 9/1976 | Boshoff | 206/223 |
| 4,153,160 | 5/1979 | Leigh | 206/370 |
| 4,293,074 | 10/1981 | Dunsky | 206/369 |
| 4,294,349 | 10/1981 | Ibsen et al. | 206/63.5 |
| 4,353,694 | 10/1982 | Pelerin | 206/370 |
| 4,364,473 | 12/1982 | Bogaert | 206/63.5 |
| 4,429,793 | 2/1984 | Ehmann | 206/570 |
| 4,522,302 | 6/1985 | Paikoff | 206/570 |
| 4,523,679 | 6/1985 | Paikoff et al. | 206/370 |
| 4,595,102 | 6/1986 | Cianci et al. | 206/370 |
| 4,596,329 | 6/1986 | Eldridge, Jr. | 206/370 |
| 4,763,791 | 8/1988 | Halverson | 206/369 |
| 4,767,008 | 8/1988 | Warnecke et al. | 206/370 |

Primary Examiner—Jimmy G. Foster
Attorney, Agent, or Firm—Brumbaugh, Graves, Donohue & Raymond

[57] ABSTRACT

Portable kits for the treatment of dental problems by persons untrained in dentistry have the instruments, medicaments and other articles required to treat specified problems carried in a tray having covered recesses sized and shaped to receive them. Step-by-step instructions for treting the problems are secured on the inner surface of a lid covering the tray so that when the lid is opened, the instructions are in view. Each item on the tray is uniquely identified, such as by letter or number, and the instructions refer to them by such indicia to avoid error. In addition, the instructions and covers for the recesses are suitably color coded to simplify following instructions. Four kits, each designed for treatment of a number of designated dental problems, are described. The kits enable emergency treatment of dental problems when travelling or when professional dental care is unavailable.

10 Claims, 4 Drawing Sheets

DENTAL TREATMENT KIT

BACKGROUND OF THE INVENTION

This invention relates to apparatus for administering dental therapy and more particularly, to kits, each including a plurality of dental instruments and materials, especially adapted to enable persons untrained in dentistry to administer dental treatment on an emergency basis or on a routine basis when professional care is inconvenient or unavailable.

Dental problems often arise when the sufferer is unable to obtain immediate treatment from a trained dentist or dental technician. When away from home, people are often reluctant to seek assistance from dentists unknown to them, preferring instead to suffer discomfort until they can see their regular dentist. In cases where the discomfort is severe, this might require curtailing a vacation or business trip to return home for treatment. It also often occurs that more or less routine dental care is delayed because of travel or unavailability of the patient's regular dental professional.

A variety of so-called "first aid" devices and medicaments are available for the home or traveler to treat minor medical conditions, such as cuts and abrasions, intestinal discomfort, headaches, etc. First aid kits of varying degrees of sophistication can be purchased or assembled to be available in anticipation of such emergencies. However, no comparable means have been available for the treatment of routine dental conditions or emergencies and victims must either suffer or seek nearby, and unfamiliar, professional help.

SUMMARY OF THE INVENTION

It is the object of the present invention to provide kits, comprising a plurality of instruments, medicaments and materials assembled especially for the administration of dental care by a person untrained in dentistry. Each of the severe kits to be described is designed to provide the means necessary to treat designated dental problems and include clear, easily understood instructions to enable identification of the problem and to treat the patient simply and effectively to attend to routine care or to relieve the attendant discomfort, until professional dental treatment can be obtained.

Each of the kits is arranged and the instructions prepared in a manner assuring proper usage by an untrained person and reducing the possibility of error to a minimum. The kits are compactly packaged, incorporating a tray having individual recesses or receptacles for the articles, each such recess being uniquely shaped or dimensioned to receive only its designated item. Transparent plastic covers are provided for the recesses to maintain cleanliness and to retain the articles in place during travel and handling. Each of the items in the tray is identified by a unique number or letter, or combination of numbers and letters, keyed to the instructions so that the user is directed to the precise instrumentality required for a particular treatment step. Moreover, the transparent covers are color coded in accordance with the particular procedure in which the articles are used. These expedients further simplify the administration of treatment by an untrained person.

Including within the various kits to be described are a number of specialized instruments, developed for use in particular designated procedures and adapted to be readily manipulated by the untrained person. These instruments enable certain procedures can be carried out on a temporary basis which later, may be permanently effected by a trained dentist with the more sophisticated professional dental equipment normally available to him.

BRIEF IDENTIFICATION OF THE DRAWINGS

The foregoing and other objects, features and advantages of the invention will become apparent from the following detailed description thereof when taken in conjunction with the appended drawings in which.

DETAILED DESCRIPTION OF THE INVENTION

Since dental problems or emergencies can arise in almost every area of dental health, the dental kits according to the invention are arranged to provide the user with the means to treat a wide spectrum of routine problems and emergencies that may be encountered. In the preferred embodiment of the invention, four separate dental health kits are provided, each kit providing the necessary instruments, medicaments and materials to treat problems in two different areas of dental health. Printed instructions are included in each kit, written, in language readily understandable by the layman, for identifying and then treating the various problems most often occurring in the particular areas of dental care for which the kit is designed.

The articles included in the kit, i.e., instruments, medicaments and materials, are arranged such that by following the step-by-step instructions included in the kit, the user will be directed to the appropriate instrument and/or material in the precise order necessary to effect the treatment and be told precisely how that instrument or material is to be used.

Figure 1:
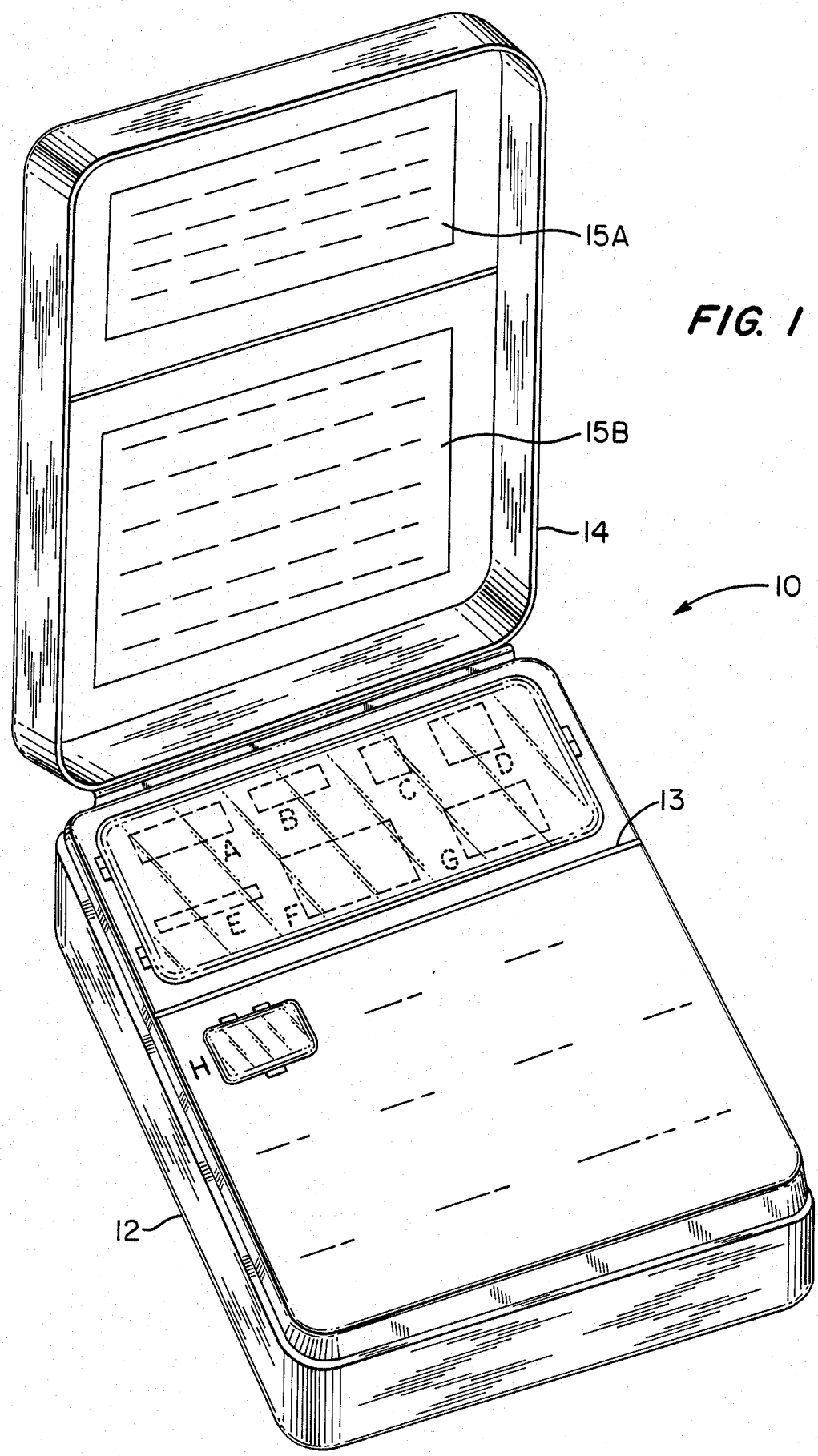
FIG. 1 is an oblique view of an assembled kit in accordance with the invention showing the overall arrangement of tray, lid and contents.

Turning now to the drawings, FIG. 1 illustrates the general form of the overall construction of a kit according to the invention. For purposes of illustration, one kit of the four contemplated by the inventors is shown in the drawings. The other kits, to be described in detail below, will be of the same overall configuration, but with differences in the instruments and materials included in the kit and their arrangement in the tray.

The basic construction of the kit 10 includes a tray portion 12 and a lid 14, both of which are formed of plastic or cardboard of sufficient rigidity and strength to hold and protect the contents. The lid 14 may be hinged to the tray along one edge thereof or may be completely separable. In either case, the lid fits snugly over the tray to aid in maintaining integrity of the kit and sterility of the contents. Preferably, the commplete kit is sealed in cellophane or equivalent plastic wrap after assembly to aid further in protecting the kit from tampering or damage.

Complete instructions, 15A, 15B, for use of the kit for the dental problems to which it is directed are printed or glued on the inside surface of the lid. This guards against loss or damage which, of its occurred, would effectively nullify the utility of the kit.

The representative kit of FIG. 1 is designed to apply to two areas of dental care, (1) Pedodonture (children's dentistry) and preventive care, and (2) General Dental Emergencies. Thus, both the tray and the lid are divided by a line into two sections, one of each of the areas to which the kit is directed.

Figure 2:
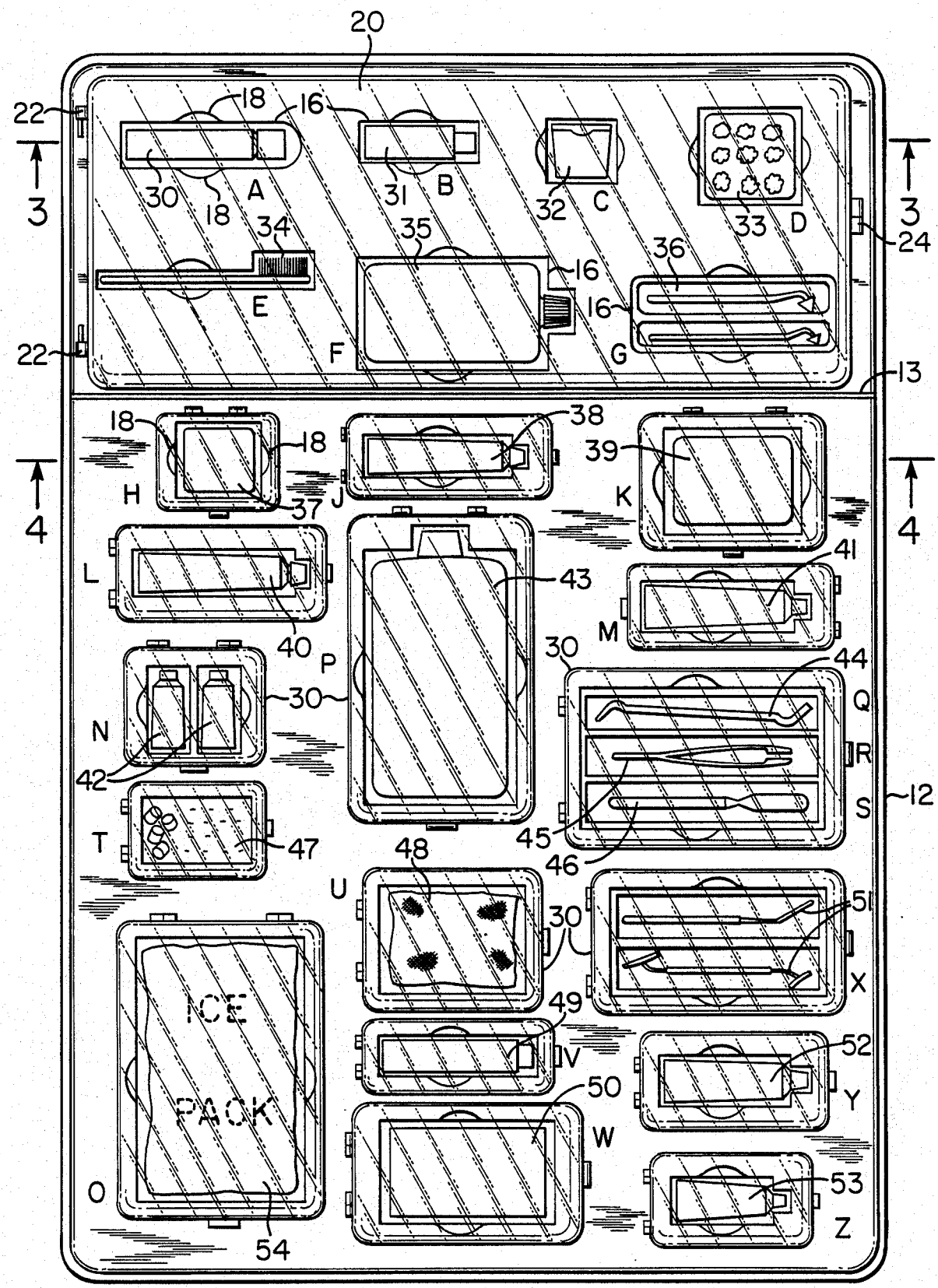
FIG. 2 is a plan view of the tray of the kit of FIG. 1 showing in detail the layout of the tray and its contents.
Figure 3:
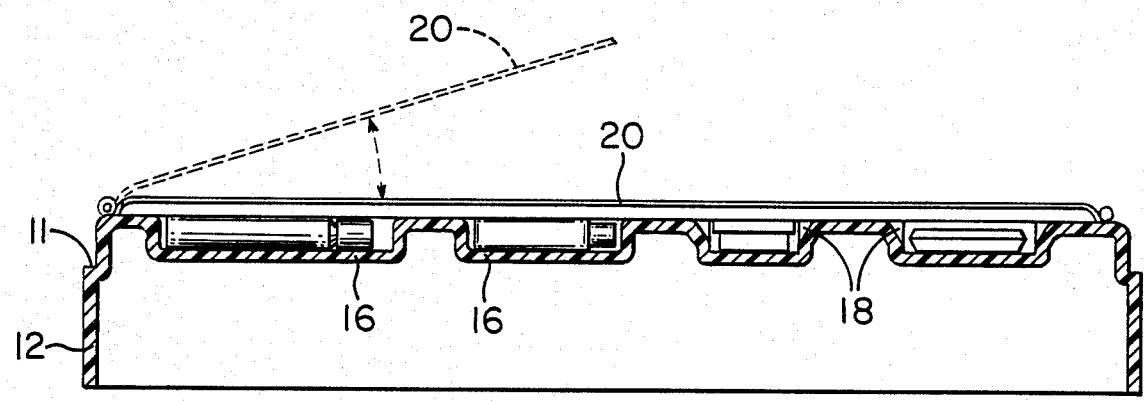
FIG. 3 is a section through the tray of FIG. 1 taken along the line 3—3, showing the receptacles for the articles and a cover for a number of receptacles.
Figure 4:
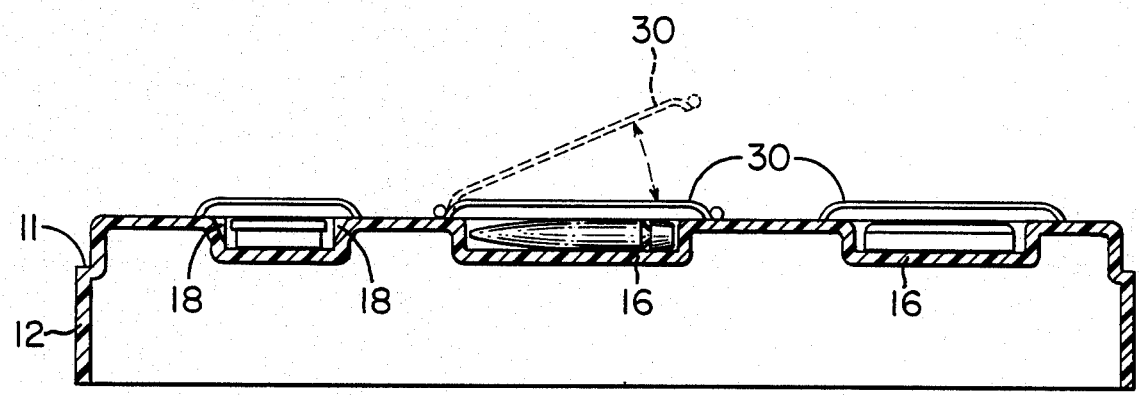
FIG. 4 is a section through the tray of FIG. 1 taken along the line 4—4, showing the receptacles for the articles and individual covers for each of the receptacles.

The layout and construction of the tray 12 for the kit of FIG. 1 is illustrated in FIGS. 2, 3 and 4. Referring to these drawings, the tray 12, which preferably is pressed or molded of plastic, is formed with a plurality of recesses 16 which serve as receptacles for the individual instruments, medicaments and materials comprising the articles of the kit. As seen best in FIG. 2, these recesses are sized and shaped to receive specific articles, to minimize the possibility of improper replacement after use and to minimize movement of the individual articles during traveling, handling, etc.

Each of the receptacles 16 preferably is provided with a pair of finger depressions 18 along opposite sides, to facilitate removing the article from the receptacle.

To assist in maintaining sterility and cleanliness of the contents and to assist in retaining the articles in their assigned recesses, releasable, resealable, covers are provided for all of the recesses. These covers are fabricated of thin, transparent plastic, visibly tinted in accordance with a prescribed color code, but allowing the contents of the recesses beneath them to be clearly visible. The covers are suitably hinged to the surface of the tray and provided with a snap closure to secure them tightly when closed. The bottom edges of the covers are provided with a sealing strip, such as soft plastic, to ensure a tight seal between the covers and the surface of the tray when closed.

A cover may be provided for each recesses individually, for groups of adjacent recesses or for all of the receptacles in a given area of the tray. By way of example, in FIG. 2, a cover 20 is shown for all of the recesses in the section of the tray above the line 13 which divides the tray contents in accordance with the two dental areas to which the kit is directed. The cover 20 is hinged at its left-hand edge (as seen in FIG. 2) by hinges 22 and secured to the surface of the tray at its opposite edge by snap clasp 24. In FIG. 3, the cover 20 is shown in solid line in its closed position. When opened, the cover 20 moves in the direction shown in schematically in dotted line in FIG. 3 and opens fully to allow ready access to all of the articles.

An alternative arrangement of covers for the recesses is shown in the portion of FIG. 2 below line 13 and in FIG. 4. In this arrangement, each of the recesses is provided with a separate cover 30 which, as in the case of the cover 20, is of thin transparent plastic tinted with a color appropriate to the color code for the particular area of treatment encompassed by the elements by the kit. As in the case of the cover 20, each of the individual covers is hinged to the surface of the tray along one side and includes a snap fastener at its opposite side to secure it to the tray surface when closed. The opening of a cover 30 is shown in dotted line in FIG. 4.

As seen best in the cross-sectional views of FIG. 3 and FIG. 4, the periphery of the tray 12 is formed with a ledge or indent 11 which provides a seart for the edge of the lid 14 when the kit is closed. This adds to the ability to seal the entire kit in the manufacturing process and upon reclosing after use. Although not shown in the drawings, suitable fasteners such as snaps, Velcro, hasps, etc. may be provided to secure the lid in its closed position when the kit is not in use.

The contents of the various kits contemplated by the invention will now be described in the context of the areas of dental care for which they are intended and the simplified instructions to be incorporated in the respective kits. As indicated above, four separate kits are presently envisioned, each directed to treatment of two different areas of dental problems. These kits are as follows:

| Kit No. 1 | Kit No. 2 |
|---|---|
| Pedodonture (children's dentistry); Preventive Dental Care | Periodonture (gum problems); Prosthetics (dentures, partial dentures) |
| Kit No. 3 | Kit No 4 |
| Restorative Problems Orthodontics (braces, etc.) | Endodonture (root canal) Surgical Emergencies |

The kit of FIGS. 1-4, while representative of all of the contemplated kits, illustrates specifically Kit No. 1, for the treatment of Pedodonture (children's dental problems) and General Dental Emergencies. Referring to FIG. 2, the upper portion of the tray (as seen in the drawing) above the transverse dividing line 13 contains the instruments, medicaments and materials for treatment of children's dental problems and for administration of preventive care for children. To distinguish those articles from others on the tray (below line 13), the cover 20 is tinted blue and the related instructions, 15A, fastened to the inside surface of the lid 14, will bear blue markings identifying it with that portion of the tray.

The section of the tray in FIG. 2 below line 13, incorporates the instruments, medicaments and materials for treatment of general dental emergencies and is assigned the color red as its color code. Accordingly, each of the covers 30 for the respective articles is tinted red and the applicable instructions 15B likewise is provided with red markings to coordinate with them.

In addition to the color coding, use of the kit is simplified by uniquely identifying each of the articles in the tray by a differentiating letter or number. In the embodiment of FIG. 2, bold, uppercase letters are used for each of the articles and these letters are similarly referred to in the related instructions. If desired, numerals or combinations of letters and numerals may be used.

Each of the four kits has its own group of instruments, medicaments and materials retained in suitably configured recesses bearing identifying letters or numbers and the respective plastic covers will be color coded appropriately. The outer surface of the lid of each of the kits will be appropriately labeled in bold print with the types of dental problems to which it is directed so that the proper kit can be readily selected for treatment of the specific problem requiring attention.

To enhance the utility of the dental kits of the invention to an untrained person and to reduce the cost of the kits, three new instruments have been devised and other instruments commonly used by professional dentists have been modified for inclusion in the kits. With respect to the latter, conventional dental instruments such as mirrors, tweezers, spatulas, and other devices, normally made of surgical steel for professional use, are made wholly or in part of plastics having suitable properties of hardness and resiliency. The use of plastics is appropriate for the kit instruments since use is limited and resterilization may effectively be done by cleaning the instruments with alcohol included in the kits, thereby avoiding the necessity for the autoclaving required in the dentist's office. It is thus possible to reduce the cost and weight of the kit instruments without impairing their utility.

Figure 5:
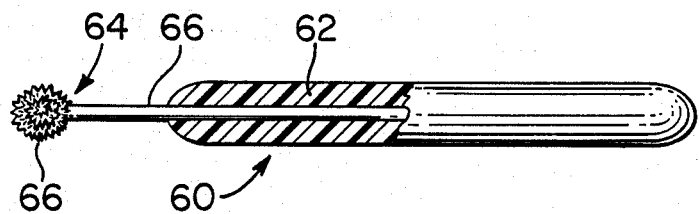
FIG. 5 illustrates a denture rongeur designed especially for inclusion in a kit according to the invention.
Figure 6:
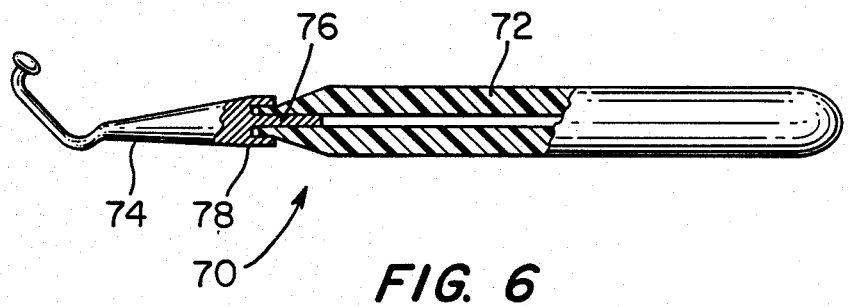
FIG. 6 illustrates a dental curette designed for inclusion in a kit according to the invention.
Figure 7:
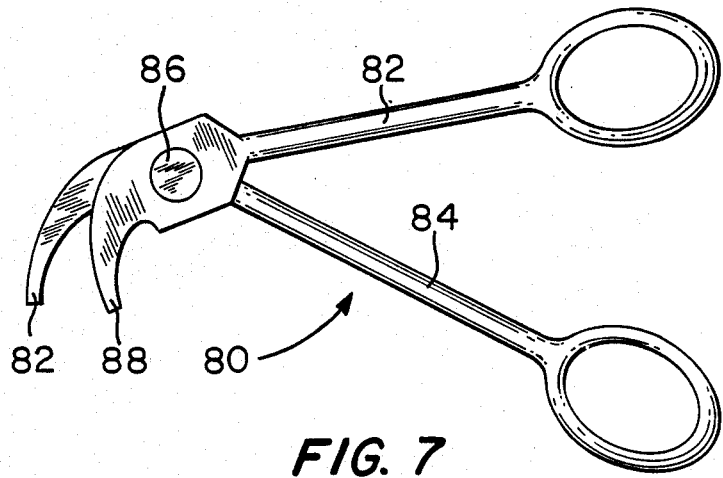
FIG. 7 illustrates a clasp adjusting instrument for partial dentures, designed especially for inclusion in a kit according to the invention.

The three newly developed instruments are illustrated in FIGS. 5, 6 and 7. The instrument 60 shown in FIG. 5 is what is referred to as a denture rongeur, which is similar to a file and is used for abrading the hard plastic material used in dental prosthesis, i.e., full or partial dentures. It often occurs that for various reasons dental prostheses become misaligned or otherwise uncomfortable in the mouth of the wearer, affecting the wearer's bite or irritating gums. In many cases, relief can be obtained by minor changes in the contour of the prosthesis. The denture rongeur of FIG. 5 is used by the untrained person in place of the motor-drive instruments available in the professional dental office.

As shown in FIG. 5, the rongeur 60 comprises a plastic handle 62 of a size and shape to be gripped comfortably by the hand, and a working element 64. The latter has an elongated shank 66 inserted longitudinally within the handle and an abrading tip 66 at its free end, the tip preferably being formed integrally with the shank and generally spherical in shape. The shank and tip of the rongeur preferably is made of surgical steel of the type normally used for dental instruments and the shank is secured within the handle by friction fit or an adhesive.

The outer surface of the tip is cut in crisscross fashion to provide an overall surface covered with small, sharp-pointed elements. As will be described more fully in connection with the instructions for Kit No. 2, reproduced hereinafter, the rongeur is used to file down high spots in a full or partial denture that cause discomfort.

The instrument 70 of FIG. 6 is a special form of curette used in perodontal treatment to dislodge food and plaque from the tooth surfaces, especially around and under the gum line. Conventional curettes are formed of a single piece of surgical steel with a bent tip at one end to facilitate reaching the tooth surfaces in the mouth. The end of the tip is slightly flattened to form a laterally extending ridge for insertion under the gum line to dislodge food and plaque.

The special curette developed for use with the dental kits of the invention comprises a plastic handle 72 of size and shape to be comfortably grasped in the hand and a separable metal tip 74. The latter includes a shank portion 76 which is received in an axial bore in the handle 72. A connector 78, such as a bayonet coupling, threads, etc., releasably couples the tip to the handle. Several replaceable tips, having different angular configurations, are included in the kit to facilitate reaching of all of the tooth and gum areas that are to be treated.

The roblem of loosened clasps on partial dentures that cause the partial dentures to move or slip out of position in the mouth, may be treated with the use of the adjustment pliers illustrated in FIG. 7. As shown, the pliers have a pair of pivotally coupled handles 82, 84 similar to the handles of a scissor. The handles extend beyond the pivot point 86 to form a pair of curved jaws 87, 88. The curved jaws of the instrument permit read access to reach the loosened clasps on a partial denture in the mouth of a patient and to reclamp them firmly to the supporting tooth structure. The reduce cost and weight, the handles and pivot of the pliers may be made of a suitably strong plastic with metal tips secured to the plastic to add rigidity and improved function.

Referring again to FIG. 2, the items included in the tray 12 are as follows:

| Ref. No. | Letter | Item |
|---|---|---|
| 30 | A | bottle of viscous zylocaine |
| 31 | B | bottle of fluoride gel |
| 32 | C | dental floss |
| 33 | D | plaque disclosing tablets |
| 34 | E | toothbrush |
| 35 | F | plax (liquid plaque remover) |
| 36 | G | rubber tipped gum stimulators |
| 37 | H | ibuprofen tablets - 200 mg. |
| 38 | J | tube of Cavit G (temporary filling material) |
| 39 | K | (antiseptic lozenges |
| 40 | L | sensodyne (desensitizing) toothpaste |
| 41 | M | tube of dry socket paste |
| 42 | N | tubes of Temp-bond (temporary dental cement) |
| 54 | O | ice pack |
| 43 | P | bottle of 90% alcohol solution |
| 44 | Q | plastic instrument |
| 45 | R | plastic tweezer (in tray) |
| 46 | S | plastic spatula |
| 47 | T | sterile cotton pellets |
| 48 | U | sterile gauze pads (1″ × 1″, 2″ × 2″) |
| 49 | V | bottle of Eugenol (oil of cloves) |
| 50 | W | pad of mixing papers |
| 51 | X | hand and dental mirrors (on tray) |
| 52 | Y | tube of topical anesthetic |
| 53 | Z | tube of Tempit (temporary dental cement) |

The user's problem guide and detailed instructions 15A, 15B, on the lid 14, are reproduced below:

| PROBLEM GUIDE - KIT I | |
|---|---|
| SYMPTOM | PRODUCT AND NUMBER |
| PEDODONTURE/PREVENTIVE CARE | |
| Teething Pain (child) | Viscous Zylocaine A |
| Prevent Decay (Preventive Care) | Fluoride Gel B |
| Dislodge Food & Help Brushing | |
| (Better Home Maintenance) | Floss C |
| | Disclosing Tablet D |
| | Brush E |
| | Plax F |
| | Stimulator G |
| GENERAL DENTAL EMERGENCIES | |
| Mild Pain/Swollen Face | Ibuprofen 4 |
| | Ice Pack 0 |
| Loose Or Missing Filling, Sensitivity, Or Sore Spots | |
| | Fluoride Gel B |
| | Cavit G J |
| | Plastic Instrument Q |
| | Sensodyne Toothpaste L |
| | Eugenol V |

-continued

PROBLEM GUIDE - KIT I

| SYMPTOM | PRODUCT AND NUMBER |
| --- | --- |
| Re-Cement Crown | Benzodent Y |
| | Tempit Z |
| | Temp Bond N |
| | Mixing Slab W |
| | Reusable Spatula S |
| Sore Throat | Antiseptic Lozenges K |
| Problems After Extraction | Dry Socket Paste M |
| | Ice Pack 0 |

INSTRUCTIONS FOR KIT I

Children's/Preventive Care—Blue Cover the Letter of the Product Corresponds to the Lettered Compartment in the Kit Under the Blue Cover A Viscous Zylocaine—For Children's Gum Pain, e.g., Teething pain (numbs gum tissue)—Keep refrigerated, if possible, but not necessary, before and after initial use. Apply gently with a cold pacifier or clean Q-tip in small amounts on child's gum before bedtime or when needed. Never apply more than twice a day.

B Fluoride Gel—Helps Alleviate Sensitivity And Hardens Tooth Structure—Apply at least one time each day. Coat affected area with cotton pellet (T) and leave on tooth. Apply especially before bedtime and do not eat or rinse thereafter.

C Dental Floss—Dislodge Food And Plaque Between Teeth—Pull floss gently through spaces between teeth; bright floss slightly below gum line to dislodge food and plaque. Hug one side of tooth with floss and then the other side of tooth for best results.

D Disclosing Tablet—Test Of Efficacy of Brushing Technique—Use after brushing. This tablet, when chewed, will temporarily leave a reddish stain on teeth, but only on the plaque that is left on teeth after brushing. This is an easy to use test of your brushing techique. Chew tablet, expectorate (spit out), and view in mirror. Little stain on teeth shows good brushing technique. Use 1 or 2 times per week.

E Tooth Brush—Only use a soft bristle for safest and most efficient results. Brush up and down, and then side to side. Always remember to be gentle. Brush gums gently as well as teeth for best results. Always use gentle strokes. Do not abrade.

F Plaque Remover—Helps Promote Cleaner Teeth—Rinse with plaque remover before brushing to help loosen debris. Then brush teeth (and gums) as described above.

INSTRUCTIONS FOR KIT I

General Emergencies—Red Covers the Letter of the Product Corresponds to the Lettered Compartment in the Kit Under the Red Covers H Ibuprofen 200 mg. Tablet—To Be Used For Mild to Moderate Pain—Take 1 tablet every 6 hours as needed. It does not contain aspirin. If adverse reaction, call a physician immediately.

J Cavit G—Use If a Filling Falls Out—Dry tooth with cotton pellet (T); use the plastic color coded tweezer (R) to hold cotton pellet (T) in place. After drying, place small amount of cavit g in hole in tooth with plastic instrument (Q). Use enough cavit g to fill tooth. Wipe off excess with plastic instrument (Q) only afting bitting down onto the cavit. Do not eat for about 15 to 30 minutes. Cavit will harden with your saliva from 15 to 30 minutes. Stay in closed mouth position, if possible, to assure proper bite.

K Antiseptic Lozenges—For minor sore throat pain, use up to 3 lozenges per day.

L Desensitizing Toothpaste (e.g., Sensodyne F)—For Sensitive Teeth—Use in place of regular toothpaste, 3 times per day, for sensitive teeth.

M Dry Socket Paste—Use if in Pain After Dental Extraction—Use 1×1 sterile gauze (U) and place small amount of dry socket paste on it. Wipe affected extraction site with this material. Material, not gauze, should be left on affected area. Use 2 to 3 times per day if needed.

N Temp Bond—To Re-cement Bridge or Crown—Mix small equal amounts (i.e., a dab) from each tube with reusable spatula (S) on mixing pad (W). Dry the inside of the crown with cotton pellet (T) and tweezer (R). Place Temp Bond in crown or bridge with end of plastic instrument (Q). Place back onto tooth. Closely firmly to set. Remain closed and let it set up for about 5 minutes. Wipe off excess with plastic instrument (Q).

Plastic Tray holds instruments Q, R. and S:

Q Plastic instrument—Use as directed as a "placement-type" instrument.

R Plastic Tweezer—Like the plastic instrument described above, use as directed as a "placement-type" instrument.

S Reusable Spatula—Use to mix any of the kit's materials. Like the kit's other instruments, it can be reused if cleaned in alcohol solution (P).

T Cotton Pellet—To dry tooth and also apply medicaments to tooth or gum tissue as directed.

U 1"×1" and 2"×2" Sterile Gauze Pads—To Dry Or Use To Apply Pressure In Mouth To Stop Bleeding—Keep gauze clean and sealed until ready for use.

V Eugenol—Use To Ease Pain—Dry tooth with tweezers #19 and cotton pellet #21. Place cotton pellet #21 in eugenol #23 and put a small amount on affected area. The pain will begin to ease. If severe pain persists, see your dentist.

W Mixing Paper Pad—Mix materials on specially coated material. To reuse, peel off top (used) piece and throw away.

X Mirrors (Two Mirrors Provided)—Place small dental mirror in front of tooth and use to best advantage as needed. Remember that light is required to view inside of mouth.

Y Benzodent (topical anesthetic)—For Sore Spot, Irritated Area, Or Canker Sore—Use tweezer R and cotton pellet T to place Benzodent on pellet. Put Benzodent on affected denture sore, canker sore, or irritated area.

Z Tempit—A tempit is used to replace missing fillings, and comes pre-mixed in a pre-loaded tube Dry tooth with cotton pellet T and tweezer R. Put tempit from tube directly in hole of tooth. Sooth down with plastic instrument Q and also use this instrument to wipe off excess. Do not eat for 30 minutes. Bite down on tooth for at least 10 minutes after tempit is applied.

O Ice Pack—Use of Swollen Face—Reusable and should be kept in freezer when not in use. With swelling, it is suggested that intermittent use is most appropriate. That is, 15 minutes on and 15 minutes off in the area of the swelling. If swelling persists, however, see your dentist. Your distist may have to recommend antibiotic treatment.

P 90% Alcohol Solution—Use to clean all instruments before replacement back into the kit.

PREVENTIVE TIPS—TOOTH TRUTHS

1. Remember, most dental problems can be avoided and prevented by your good home care.
2. Brush your teeth after each meal, floss daily, however.
3. Use a toothpaste with fluoride in it. Look for the ADA seal on the tube.
4. Eat Nutritious food; keep junk food to a minimum; gooey goodies are baddies.
5. Baby teeth are very important; they should be cared for just as adult teeth are.
6. Gum disease, not decay, is the major cause of adult tooth loss; thankfully it's preventable.

In addition to Kit No. 1 illustrated and discussed above, three other kits are presently contemplated, each directed to particular dental emergencies. As with Kit No. 1, Kit Nos. 2, 3, and 4 each comprises a package consisting of a tray and lid, with the tray having recesses sized and shaped to receive the specific articles selected for treatment of the designated emergencies. Also, as in Kit No. 1, each of Kits Nos. 2, 3 and 4 comes with its own set of Problem Guides and Instructions for the user. Following, for each of Kits Nos. 2, 3 and 4 are (a) Contents List, (b) Problem Guide and (c) Instructions:

KIT 2 - PERIODONTURE/PREVENTIVE - WHITE CODE PROSTHETICS - GREEN CODE

CONTENTS

Glyoxide - 1 tube
Curette - 5 disposable metal tips (FIG. 6)
Tooth Brush
Proxy Brush
Stimulator
Explorer
Dental Floss - in dispenser
Disclosing Tablets - 10 tablets
2 × 2 Sterile Gauze
Two Mirrors
Benzodent - 1 tube
Color Transfer Applicators - 10 dyed-end sticks
Fitt (Functional Impression Temporary Toner) - (Cushion Liner) - 5 disposable mixing cups
Cyanoacrylic Cement - 1 tube
  Plastic Tray (for organization of instruments):
Denture Rongeur (FIG. 5)
Adjustment Pliers (for clasps) (FIG. 7)
Reusable Spatula
Explorer - metal tip
Efferdent - 1 box
Fixadent - 1 tube
Temp-Bond - 2 tubes
Mixing Pads
90% Alcohol Solution - 1 bottle

PROBLEM GUIDE - KIT 2

PERIODONTURE/PREVENTIVE

| SYMPTOM | PRODUCT |
|---|---|
| Sore or Swollen Gum Tissue | Glyoxide |
|  | Curette |
| Preventive Care | Tooth Brush |
|  | Proxy Brush |
|  | Stimulator |
|  | Dental Floss |
|  | Disclosing Tablet |

PROSTHETICS

| SYMPTOM | PRODUCT |
|---|---|
| Soreness from Denture or Partial | Benzodent |
|  | Color Transfer Applicators |
|  | Denture Rongeur |
| Soft Cushion - Bad Fitting Partial or Denture | Fitt (Kerr) |
|  | Fixadent |

KIT 2 - PERIODONTURE/PREVENTIVE - WHITE CODE PROSTHETICS - GREEN CODE —continued

| | |
|---|---|
| Repair cracked dentures, broken off teeth, or plastic (acrylic) | Cyanoacrylic cement |
| Adjust partial for more retention | Partial Plier Adjuster |
|  | Fixadent |
| Clean dentures | Efferdent |
| Re-Cement crowns or bridges | Temp-Bond |

INSTRUCTIONS FOR KIT 2

Periodonture/Preventive—White Code

Glyoxide—Irrigation of Gum Tissue—Swish around throughout the mouth for one minute letting the tongue push this medication into and around the gum tissue. Spit out the glyoxide—Do not (a) swallow, (b) rinse with water, or (c) eat for 30 minutes.

Curette (with metal tips)—Dislodge Food and Plaque—Gently clean slight under gum tissue (approximately 2 mm). This will dislodge food and plaque. If gum tissue is swollen, we recommend that a dentist be seen. Use curette completely around circumference of tooth (inside and outside) and gently beneath gum tissue.

Tooth Brush—A soft bristle brush has been chosen for best overall results. Carefully brush teeth up and down and from side to side. Also brush gum tissue in a relaxed and gentle fashion.

Proxy Brush—Gently massage gum tissue between the teeth in order to help promote the health, and resistance to disease, of your gum tissue.

Stimulator—In addition to the proxy brush, use the stimulator to massage gums to ensure healthy gum tissue.

Explorer—Reference Point Instrument—Carefully use metal tip to locate a spot or reference point in mouth in need of attention. The explorer acts as a pick and should not be used in place of a curette. The explorer is exclusively used to locate a particular area.

Dental Floss—Dislodge Food and Daily Home Maintenance—Gently pull floss through the spaces between the teeth going slightly below gum tissue to dislodge food and plaque. For best results, hug one side of tooth and then hug the other side.

Diclosing Tablets—Use 1 tablet after brushing, tablet will temporarily leave a reddish stain on teeth but will only stain the plaque that is left on teeth. This is a test of your all-important brushing technique. Chew tablet, expectorate (spit out), and look in the morror. Use the disclosing tablet before bedtime about once or twice a week. Remember that the more stain you find, the more plaque you have, and the better and more frequently you must brush your teeth to maintain their health.

2×2 Sterile Guaze Pad—Use To Dry Or To Apply Pressure In Mouth—Use as directed in previously discussed steps or with curette to clean off instruments.

Mirror'Use mirror to help you to see better in your mouth. Use all available light. Use the small dental mirror in order to see the inside and outside of a tooth.

INSTRUCTION FOR KIT 2

PROSTHETICS—GREEN CODE

Benzodent—Sore Or Irritated Areas—Place small amount on Q-Tip and put directly on sore spot in mouth. If necessary, apply 3 times per day.

Color Transfer Applicators—Used To Remove Sore Spots in Mouth—Remove denture or partial and dip tip (blue area) of applicator in water; place tip directly on sore spot in mouth. The dye will not be on the sore spot. Put denture or partial back in mouth and bit down. Remove denute or partial and look inside; the blue dye mark inside denture or partial will show exactly the spot that must be filed down with denture rongeur.

Fitt (Kerr)—Relining material For Denture or Partial Denture—Contains: (a) 5 premeasured disposable clear or plastic cups, (b) eye-dropper, (c) liquid, and (d) powder. Place 10 drops of liquid using eye-dropper into a premeasured disposable clear plastic cup. Slowly add powder to liquid. Mix together with reusable spatula to a thick honey-like consistency. If added thickness is needed, add more powder to the liquid. If too thick, add a couple of addition drops of liquid. Place Fitt (Kerr) material using spatula all over the inside of the denture or partial. Make such that the entire surface and sides are covered with a thin layer. Quickly place denture or partial in mouth and bite down for 10 to 15 minutes. Trim excess on outside of denture or partial with explorer after approximately 15 minutes of setting time.

Cyanoacrylic Cement—Use to repair or re-cement acrylic found in a denture or partial or in the loss teeth of a denture or partial. Do not get cement on hands. Place small amouns where needed with tip or explorer. Hold in place for about 5 minutes. Total setting time is 15 minutes.

Plastic Tray—Holds the following Instruments:

Denture Rongeur—To Reduce Sore Spot in Denture or Partial—The dental rongeur has been developed specifically for this kit and should be used as follows: With a cutting (back and forth) motion, file sore spot (dyed area on denture or partial, see above) using medium pressure. You will see plastic filings where reduced is being done to the denture or partial. This instrument is sharp and should be used with care.

Partial Plier Adjuster—Very gently apply slight inward pressure with plier in same direction clasp is already twisted. Slight pressure with these specifically designed pliers will greatly increase retention. BE CAREFUL Clasp is very brittle so that you must apply only gentle inward pressure.

Reusable Spatula—Use To Mix Various Materials—Clean often with 90% alcohol solution so that spatula can be reused.

Explorer—Use metal tip to gently locate a spot of reference. Explorer can also be used to trim excess cushion liner or cement (e.g., Fitt (Kerr).

Efferdent—Full Or Partial Denture Cleaner—Drop 1 tablet into very warm water. Put in a partial or denture and allow to soak for 10 to 12 minutes. Rinse partial or denture thoroughly with water.

Fixadent—Denture Or Partial Adhesive—Wet denture or partial and then place 5 large drops of Fixadent evenly throughout denture or partial. Immediately place in mouth so that retention will be maximized.

Temp-Bond—Re-Cement Crown Or Bridge—use equal amounts (a large dab) from tube A and tube B. Mix the equal amounts with reusable spatula on mixing slab. Dry inside of crown or bride with 2×2 gauze. Place temp-bond in crown or bridge with end of reusable spatula. Place back onto tooth. Close firmly to seat. Remain closed and let it set for 5 minutes. Wipe of excess with explorer. All of the needed instruments are found in tray.

Mixing Pads—Coated paper pad is used as the surface upon which to mix materials. To reuse, peel off used sheed and discard, leaving fresh top sheet.

90% Alcohol Solution—Use to clean instruments before they are returned to the kit.

---

KIT 3 - RESTORATIVE - BLACK CODE
ORTHODONTICS - PINK CODE

CONTENTS

2 Mirrors
Cavit G - 1 tube
Plastic Tray (for organization of instruments)
Explorer
Plastic Tweezers - Color Coded
Reusable Spatula
Disposable Mixing Sticks - 10
Plastic Instrument
Tempit - 1 tube (pre-mixed)
Mixing Pads
Sealed Sterile Cotton Pellets
Ibuprofen 200 mg Tablets - 1 bottle
Orthodontic Soft Pink Wax - 1 box
Benzodent - 1 tube
Dental Floss - in Dispenser
Glyoxide - 1 tube
90% alcohol solution - 1 bottle

PROBLEM GUIDE - KIT 3
RESTORATIVE

| SYMPTOM | PRODUCT |
| --- | --- |
| Missing fillings | Cavit G |
|  | Tempit |

ORTHODONTICS

| SYMPTOM | PRODUCT |
| --- | --- |
| Mild Pain | Ibuprofen Tablet 200 mg |
| Irritated Gums from Wearing Brace | Orthodontic Pink Wax |
| Irritated Gum Tissue Or Sore Spot | Benzodent |
|  | Dental Floss |
|  | Glyoxide |

---

INSTRUCTIONS FOR KIT 3

(Restorative—Black Code)

Dental Mirrors—Use mirros to help you to see in your mouth. Use all available light. Use small dental mirror in order to see inside and outside of tooth.

Cavit G—Replacing Missing Filling—Before filling tooth, dry tooth with cotton pellet using tweezers to do so. After drying tooth, place small amount of Cavit in hole of tooth with plastic instrument. Wipe off excess with plastic instrument after biting down on the Cavit. Do not eat for about 15 minutes; Cavit will harden with saliva in about 15 to 30 minutes. Stay in bite-down-position, as long as possible, to ensure that your bite will be correct.

Plastic Tray holds the following instruments:

Explorer—Gently use metal tip to locate a spot of reference; explorer acts as a pick to be used to locate a particular problem or area.

Tweezers—use to hold materials (e.g. cotton pellet) as directed.

Reusable Spatula—used as a placement instrument as directed.

Disposable Mixing Sticks—used as a placement instrument as directed in these instructions Plastic Instrument—used as a placement instrument as directed.

Tempit—To Replace Missing Fillings—Tempit comes pre-mixed in a pre-loaded tube. Dry tooth with cotton pellet and tweezers. Place tempit directly in tooth with tube, smooth down with plastic instrument, and wipe off excess also with plastic instruction. Bite down immediately to adjust bite. Tempit will harden with saliva. Do not eat for at least 30 minutes. Stay in bite-down position for about 10 minutes after placement of tempit.

Mixing Pads are pads of specially coated paper that are used to mix materials on. To reuse, peel off top piece and discard, leaving fresh top sheet.

Cotton Pellets—helps dry tooth and is used to place medicaments in tooth as directed.

Ibuprofen tablet 200 mg—1 tablet every six hours as needed. It contains no aspirin and is used for mild pain. If an adverse reactin occurs, call your physician.

INSTRUCTIONS FOR KIT 3

(Orthodontics—Pink Code)

Orthodontic Pink Wax—For Irritations Due To Braces—Place small amount on orthodontic wire to ease irritation. Try to wedge wax into wire for better retention. Orthodontic pink wax is very soft and moldable.

Benzodent—Sore Spots Or Irritated Tissue—Put small amount of benzodent on a Q-tip and apply directly on sore spot in mouth 3 times per day if necessary.

Dental Floss—Dislodge Food Between Teeth—Gently pull floss through space between teeth going slightly below gum line to dislodge food and plaque. Hug one side of tooth and then the other side of tooth for best results.

Glyoxide—is used to help irritated gums especially when braces are worn. Swish glyoxide throughout mouth for 1 minute letting tongue push medication into and around gum tissue. Expectorate (spit out) the glyoxide being careful not to swallow and do not rise with water. Also do not eat for 30 minutes after using glyoxide. Use twice a day (morning and evening) after brushing.

90% Alcohol Solution—to clean all instruments after use so that they can be reused. Use 90% alcohol solution on all instruments before they are returned to the kit.

---

KIT 4 - ENDODONTURE - ORANGE CODE
SURGICAL EMERGENCIES - YELLOW CODE

CONTENTS

Ibuprofen Tablets 200 mg - 1 bottle
Eugenol - 1 bottle
Fluoride Gel - 1 tube
Tempit - 1 pre-mixed tube
Cotton Pellets
Plastic Tray (for organization of instruments)
Explorer
Reusable Spatula
Tweezers
Dry Socket Paste - 1 tube
Cotton Pellets
Tweezers
Eugenol - 1 bottle
Tannic Acid - 10 tea bags
2 × 2 Sterile Gauze Pads
Reusable Ice Pack
90% Alcohol Solution - 1 bottle

---

-continued

KIT 4 - ENDODONTURE - ORANGE CODE
SURGICAL EMERGENCIES - YELLOW CODE

PROBLEM GUIDE - KIT 4
ENDODONTURE

| SYMPTOM | PRODUCT |
|---|---|
| Pain | Ibuprofen |
|  | Eugenol |
| Irritation | Fluoride Gel |
| Missing Filling | Tempit |

SURGICAL EMERGENCIES

| SYMPTOM | PRODUCT |
|---|---|
| Pain | Dry Socket Paste |
| Stop Bleeding | Tannic Acid |
|  | 2 × 2 gauze |
| Swelling | Ice Pack |
|  | Special Bleeding Instructions |

INSTRUCTIONS FOR KIT 4

(Endodonture—Orange Code)

Ibuprofen Tablet 200 mg—Mild Or Moderate Pain—Take 1 tablet every 5 to 6 hours only if necessary for mild to moderate pain. It contains no aspirin. If adverse symptoms result, call your physician.

Eugenol—To East Pain—Dry tooth with tweezers and cotton pellet. Dip cotton pellet in small amount of eugenol and plce on affected area in and around tooth. This will temporarily ease pain. If the pain is severe or persistent, see a dentist for professional help.

Fluoride Gel—For Preventive Fluoride Or Sensitive Teeth—Apply on teeth 1 or 2 times per day (morning/evening). Apply fluoride gel with cotton pellet. Fluoride gel will penetrate and harden the tooth structure. Do not rise or drink after application for 60 minutes.

Tempit—is used to replace missing fillings and comes in a pre-mixed, pre-loaded tube. Dry tooth with cotton pellet and tweezers. Place tempit directly in tooth with tube and smooth down with reusable spatula. Wipe of excess around tooth with either explorer or reusable spatula. Bite down immediately to adjust bite. Tempit will harden with saliva. Do not eat for approximately 30 minutes. Stay in bite-down-position to adjust bite for at least 10 minutes.

Cotton Pellets—are used to dry teeth and apply medicaments.

Plastic Tray holds the following instruments:

Explorer—Gently use metal tip to locate a point of reference.

Reusable Spatula—is used as a placement instrument.

Tweezers—are used to hold and place items such as cotton pellets.

INSTRUCTIONS FOR KIT 4

(Surgical Emergencies—Yellow Code)

Dry Socket Paste—For Pain After Extraction—Gently dry the extraction site with a 2×2 sterile gauze pad. Put a medium amount of dry socket paste on a cotton pellet with tweezers. Place paste directly on extraction site in mouth. Use up to 3 times per day for relief. If pain is severe, see your dentist.

Cotton Pellets—are used to dry and then apply different materials.

Tweezers—act as a placement instrument.

Eugenol—Use To Ease Pain—Dry tooth with tweezers and cotton pellet. Place cotton pellet in Eugenol and put a small amount on affected area. The pain will begin to ease. If severe pain persists, see your dentist.

Ibuprofen table 200 mg—For Mild To Moderate Pain—1 tablet every 6 hours for mild to moderate pain. Ibuprofen contains no aspirin. If you experience adverse symptoms, call your physician.

Tannic Acid—To Stop Bleeding—Place a wet tea bag (contains tannic acid) in mouth on extraction site and bite down with moderate pressure. Tannic acid will help coagulate (stop) bleeding. Change tea bag, if needed, every 10 minutes. If bleeding stops, bite down on a 2×2 gauze pad.

2×2 Gauze Pad—To Stop Bleeding—will also coagulate (stop) bleeding with applied pressure.

Ice Pack—To Reduce Swelling—Reusable ice pack should be kept in freezer when not in use. Place ice pack on swollen area; use intermittently, namely, 15 minutes on and 15 minutes off. We always recommend that you see a dentist when swelling occurs. The dentist may recommend an antibiotic plus other additional treatments.

90% Alcohol Solution—Is used to clean all instruments after use and before being returned to the kit.

SPECIAL BLEEDING INSTRUCTIONS

Care of the Mouth after Extraction

DON'T RINSE mouth for 24 hours.

2. KEEP FINGERS AND TONGUE away from socket.
3. BLEEDING. Some bleeding following tooth extraction is to be expected. If unusual, place a sterile gauze pad firmly over the place of extraction, and bite down or hold in place with pressure for 10 minutes. Repeat if necessary. Avoid hot liquids.
4. SWELLING. Use ice pack or towl wrung out of ice water against cheek for 15 minutes. Repeat half hour later. Swelling may start after tooth has been removed but is no cause for alarm.
5. FOOD. Light diet is advisable during first 24 hours.
6. NEXT DAY rinse mouth with ½ teaspoonful of salt in glass of warm water.
7. BONY EDGES. After teeth are extracted, the patient may feel hard projections in the mouth and think they are roots. This is usually the hard, bony partition which surrounds the roots of the teeth. These generally break away or work themselves out.
8. In case of unusual disturbance or questions, call your dentist.

While four kits contemplated by the inventors have been described in detail, it will be apparent that additional kits may be devised on accordance with the invention and that the four kits described may be divided into smaller kits of more limited application if desired. Other variations may occur to those skilled in the art within the scope of the invention as set forth in the appended claims.

We claim:

1. A portable kit for treatment of a specified dental condition by a person untrained in dentistry comprising:
   a plurality of instruments and medicaments each serving a particular function in the treatment of the specified dental condition;
   printed instructions describing said dental condition and specifying, in order of implementation, the steps to be taken in treating said condition, said instructions relating said instruments and medicaments to said steps;
   a tray having a plurality of recesses for holding said instruments and medicaments, each of said recesses being sized and shaped to receive a particular one of said instruments and medicaments;
   a cover for each of said recesses releasably secured to said tray to permit selective access to said instruments and medicaments;
   indicia affixed to said tray adjacent each recess uniquely identifying each of said instruments and medicaments, said instructions referring to said indicia in specifying the steps to be taken in treating the specified emergency; and
   a lid for enclosing said tray, said instructions being carried on the inner surface of said lid to be exposed to view when said lid is opened.

2. The kit of claim 1 wherein an arbitrarily selected color is associated with said dental condition and wherein said printed instructions are marked with said color and the covers are of said color.

3. The kit of claim 1 above wherein said covers are transparent.

4. The kit of claim 1 above wherein a single transparent cover is provided for a plurality of said recesses.

5. The kit of claim 1 above wherein a separate transparent cover is provided for each of said recesses.

6. A portable kit for treatment of groups of specified dental conditions by a person untrained in dentistry comprising:
   a plurality of instruments and medicaments each serving a particular function in the treatment of one or more of said specified conditions;
   printed instructions separately describing each of said dental conditins and specifying, in order of implementation, the steps to be taken in treating each of said conditions, said instructions relating said instruments and medicaments to said steps;
   a tray for holding said instruments and medicaments, said tray being divided into separate sections, each associated with one of said groups of dental conditions, each of said sections being recessed for holding the instruments and medicaments selected for treatment of a designated group of dental conditions, each of said recesses being sized and shaped to receive a particular one of said instruments and medicaments;
   a cover for each of said recesses releasably secured to said tray to permit selective access to said instruments and medicaments;
   indicia affixed to said tray adjacent each recess uniquely identifying each of said instruments and medicaments, said instructions referring to said indicia in specifying the steps to be taken in treating the specified condition; and
   a lid for enclosing said tray, said instructions being carried on the inner surface of said lid to be exposed to view when said lid is opened.

7. The kit of claim 6 above wherein an arbitrarily selected different color is associated with each of said groups of dental conditions and wherein the printed instructions related to each of said groups are marked with said color and the covers for the recesses in the section of the tray related to said group are of the same color.

8. The kit of claim 6 above wherein said covers are transparent.

9. The kit of claim 6 above wherein a separate transparent cover is provided for each of said recesses.

10. The kit of claim 6 above wherein a single transparent cover is provided for all of the recesses in a section of said tray.

* * * * *